(12) United States Patent
Rizzo

(10) Patent No.: US 7,267,664 B2
(45) Date of Patent: Sep. 11, 2007

(54) SELF-LOCKING SAFETY DISPOSABLE SYRINGE WITH NEEDLE PROTECTION AFTER USE

(75) Inventor: Alberto Rizzo, Lucca (IT)

(73) Assignee: RMB Ergon S.R.L., Capannori (Lucca) (IT)

( * ) Notice: Subject to any disclaimer, the term of this patent is extended or adjusted under 35 U.S.C. 154(b) by 29 days.

(21) Appl. No.: 10/988,696

(22) Filed: Nov. 16, 2004

(65) Prior Publication Data

US 2005/0124934 A1 Jun. 9, 2005

(30) Foreign Application Priority Data

Dec. 3, 2003 (IT) .......................... PR2003A0105

(51) Int. Cl.
*A61M 5/00* (2006.01)
(52) U.S. Cl. ....................................................... 604/110
(58) Field of Classification Search ................ 604/110, 604/181, 187, 263, 192–198; 128/919
See application file for complete search history.

(56) References Cited

U.S. PATENT DOCUMENTS 5,084,029 A 1/1992 Nacci née Tagliaferri et al.
5,114,404 A * 5/1992 Paxton et al. ................ 604/110
5,190,526 A * 3/1993 Murray et al. ............... 604/110
5,222,943 A 6/1993 Mazzara
5,378,240 A 1/1995 Curie et al.

FOREIGN PATENT DOCUMENTS

WO WO 00/18454 4/2000

* cited by examiner

*Primary Examiner*—Matthew F. DeSanto
(74) *Attorney, Agent, or Firm*—Young & Thompson

(57) ABSTRACT

The invention refers to the field of self-locking safety disposable syringes with needle protection after use. The syringe comprises a hollow barrel (1) ending on its lower side with an internal seat (2) adapted to receive a hub (3) carrying a cannula (4). A hollow driving rod (5) adapted to house a spring (6) is inserted in the hollow barrel. Such rod is closed at its lower end by an extracting element (8) that can slide into the hollow driving rod. The extracting element has an annular notch (9) in which a sealing ring rubber gasket (10) is housed that seals the internal wall of the hollow barrel (1). The extracting element (8) with related sealing ring gasket (10) form a liquid sucking and compressing plunger.

7 Claims, 4 Drawing Sheets

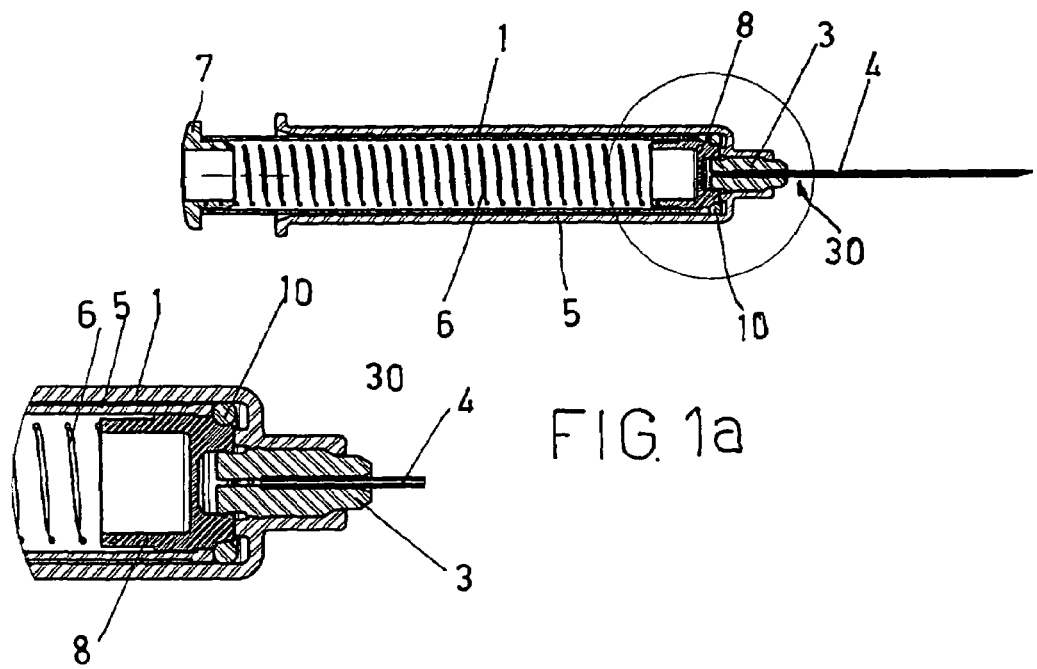
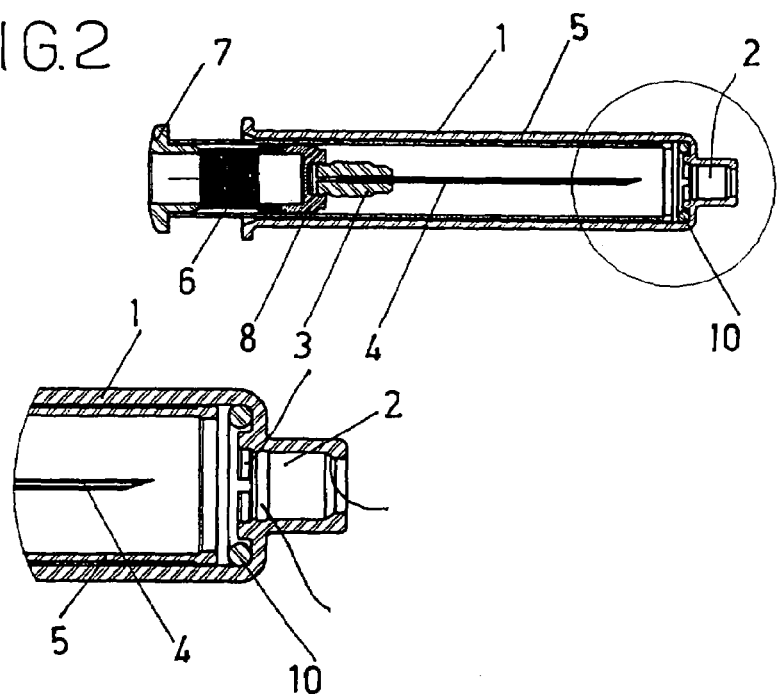

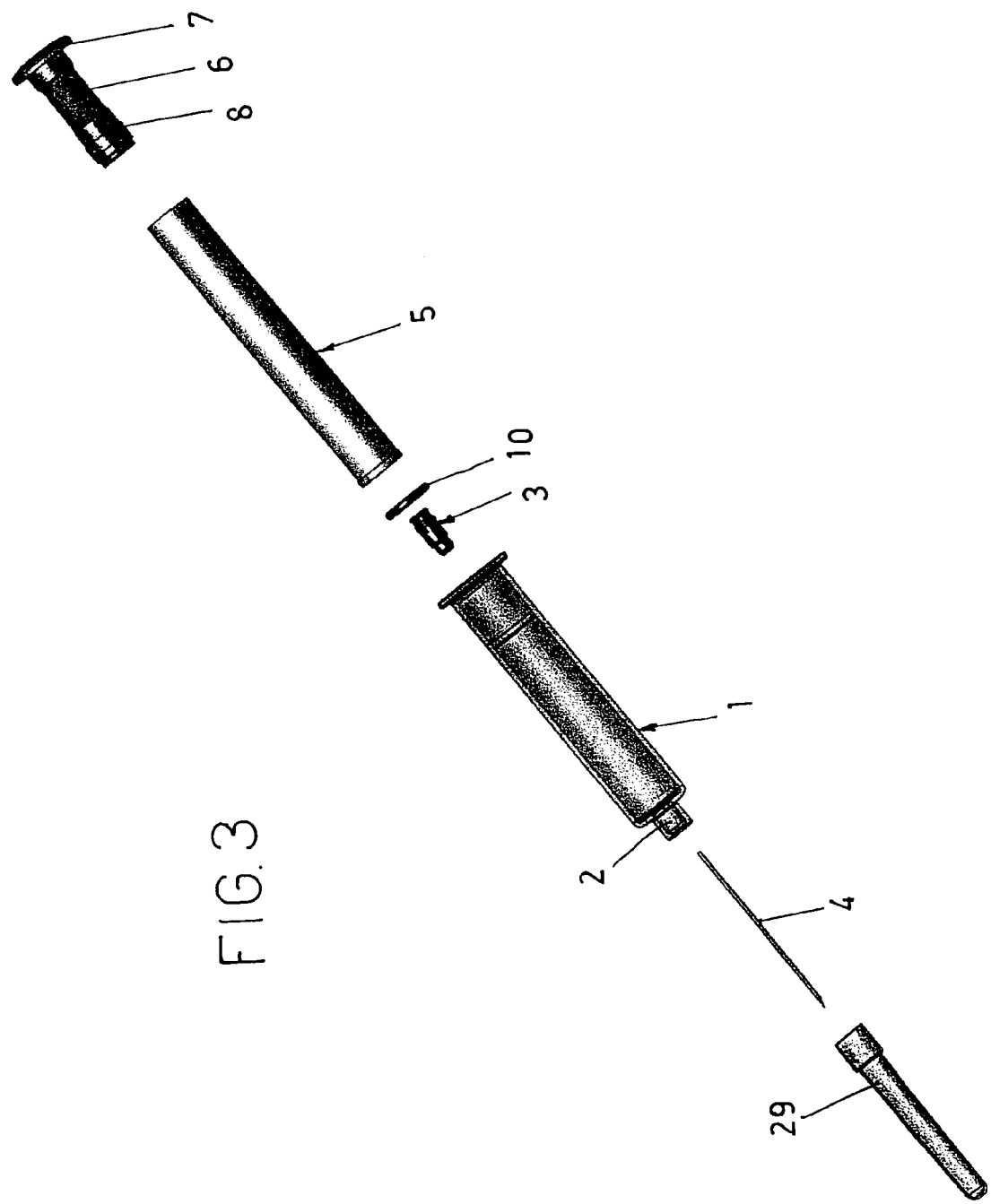

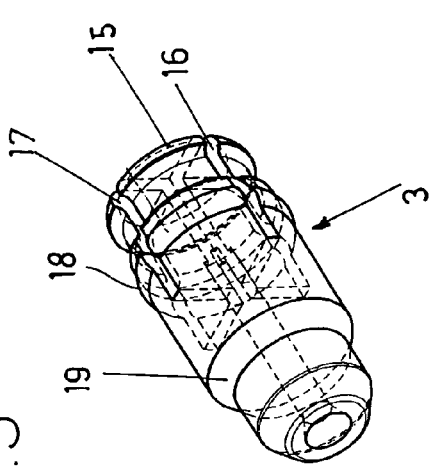
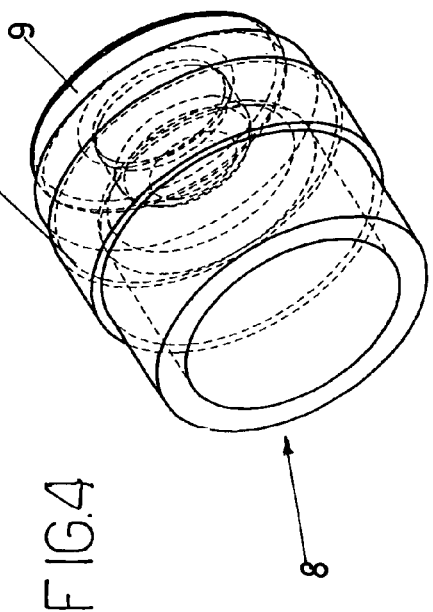
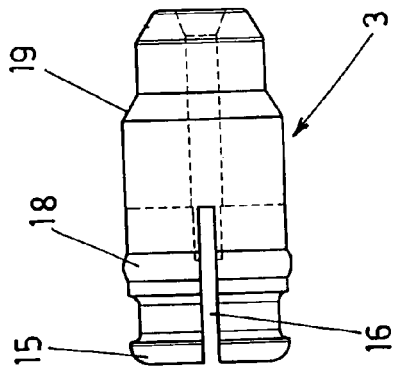
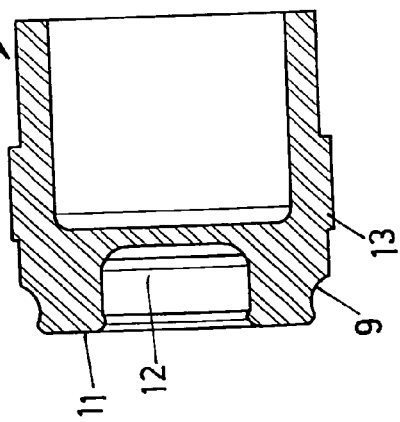

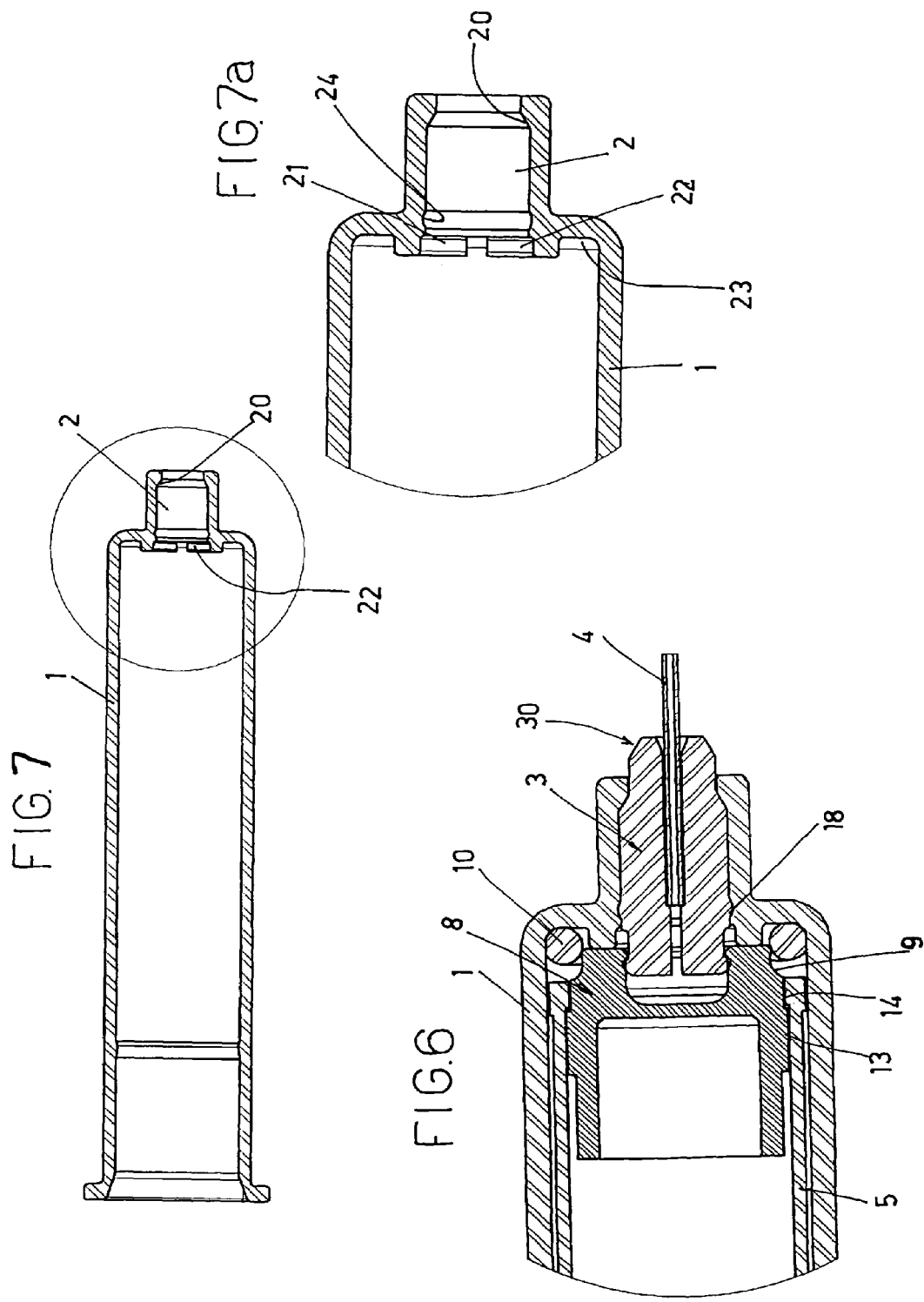

SELF-LOCKING SAFETY DISPOSABLE SYRINGE WITH NEEDLE PROTECTION AFTER USE

The present invention deals with a self-locking safety disposable syringe with needle protection after use.

More precisely, it refers to a syringe that, at the end of a normal injection of a drug, retracts its needle inside its own cylindrical hollow plunger to protect the healthcare workers from dangerous accidental needle-sticks.

The needle positioning after its use, in a place where an user cannot access it, such as inside its own hollow plunger, definitely locks the syringe making it unusable.

Different types of self-locking safety syringes are known, but the present invention refers to the type of syringe described in U.S. Pat. No. 5,222,943A that provides for a hollow syringe barrel ending with an internal seat in which a hub is housed, to which the cannula is applied. Cannula and hub form the needle.

Inside the hollow barrel, a rubber gasket for pharmaceutical use slides and it is assembled on the end of the hollow driving rod.

In the driving rod cavity, a recovery spring is assembled. This spring is connected on one side to an extractor that can pass through an axial hole passing through the rubber gasket and on another side to a plug applied at the free end of the rod. The extractor is equipped with a hooking head for the cannula-holding hub.

The above briefly described syringe has three major defects that strongly limited its use:
1) when aspirating the liquid, the rubber gasket for pharmaceutical use had a limited seal allowing external air (therefore non sterile) to enter inside the syringe and in contact with the drug to be injected;
2) when perforating the small rubber plug of a small bottle of powdery drug, to be made soluble with bi-distilled water, the necessary effort for penetrating the needle tip could disengage/detach the cannula-holding hub from its seat obtained in the initial internal part of the barrel, making the syringe completely unusable;
3) at the end of the injection, sometimes, the cannula-holding hub was not able to be detached from its initial internal part of the barrel, preventing the needle (namely the cannula-holding hub completed with cannula) from going back into its own hollow driving rod.

The first defect is due to the shape and position of the rubber gasket that has a central hole to allow the extracting element with recovery spring, when it is hooked to the cannula-holding hub, to drag the cannula-holding hub inside the hollow driving rod after its use. In fact, the sealing rubber gasket cannot clamp too tightly the extracting element with recovery spring because this would impede it from sliding and its passage necessary to take the needle inside the hollow plunger driving rod.

Moreover the depression created inside the syringe when aspirating a liquid tends to enlarge the circular lip of the rubber gasket that abuts against the extracting element, favouring the air suction and therefore increasing such inconvenience.

The second defect is due to the fact that the cannula-holding hub is inserted as a plug into the internal cylinder seat and is kept there only by a simple interference between the two plastic surfaces. Therefore, an anomalous needle penetration effort, for example on the small rubber plug of a small bottle, due to a wrong needle perforating position, detaches the hub from its internal barrel seat, totally breaking the syringe before its use.

The third defect is due to the fact that the needle does not always, at the end of the injection, go back into the hollow driving rod of the syringe to protect the healthcare worker from accidental needle-sticks. In fact, since the cannula-holding hub is kept into its internal seat of the hollow barrel only by the simple interference of the two plastic surfaces with minimum contact tolerances, a small error when manufacturing the two pieces (such manufacturing being performed with hydraulic presses for injection moulding) produces components that are too much mutually constrained.

Components that are too much constrained whose separation is derived by the efficiency of a small spring, whose force cannot be increased because the maximum size of the spring itself depends on the internal sizes of the hollow driving rod.

In addition to the three above-mentioned design defects, the syringe disclosed in U.S. Pat. No. 5,222,943A patent has a further defect since it is not conventional in using its own self-locking safety system that can mislead the end user or healthcare worker.

In fact, the nurse, at the end of the injection, in order to withdraw the needle into its protected rest position, must make the syringe plunger perform two consecutive noisy clicks.

With the first click, already provided for, the mushroom-shaped hooking head of the sliding extracting element must enter, becoming constrained, into the recess with an annular projection of the cannula-holding hub.

With the second click, that is not automatic and requires more force to press, the peripheral step on the sliding extracting element must distort and break a shoulder collar obtained inside the hollow driving rod in order to allow the recovery spring to go back and drag the needle to its safety position.

Logically the healthcare worker that uses the safety syringe as a normal disposable syringe (without a careful reading of the instructions for use), after having performed the first click, having heard the noise, and having made certain that the needle always remains in its operating position, namely has not gone back in, does not perform (due to ignorance) the second click that would have taken the needle into its protected position.

Therefore, the healthcare worker dangerously puts the protection cap back onto the pointed needle and discards the syringe deeming that its safety mechanism is not functioning.

The goal of the present invention is to remove the three severe defects that make this type of self-locking syringes not completely reliable and to simplify the utilization of the safety mechanism.

This goal is totally fulfilled by the self-locking safety disposable syringe with needle protection after its use, subject of the present invention, that is characterised in what is provided by the below-listed claims.

The characteristics and advantages will be better pointed out by the following description of a preferred embodiment shown, merely as a non-limiting example, in the enclosed tables of drawing in which:

FIGS. 1 and 1a respectively show the syringe in a longitudinal section ready for use and an enlarged part thereof;

FIGS. 2 and 2a respectively show the syringe in the same section as of FIGS. 1 and 1a, after its use with the completely-retracted needle in its safety position;

FIG. 3 shows the syringe in an exploded perspective view;

FIGS. 4, 4a and 5, 5a respectively show in a perspective view and in a longitudinal section and front view two syringe parts and more precisely the extracting element and the cannula-holding hub;

FIG. 6 shows, in an enlarged longitudinal sectional view, a particular of the syringe in order to point out some parts thereof;

FIGS. 7 and 7a shows in a longitudinal section the external hollow syringe barrel and an enlarged part thereof.

With reference to the figures, 1 designates a hollow barrel open at its top and ending at its bottom with an internal seat 2 in which a hub 3 is inserted. The hub 3 holds a cannula 4.

Hub and cannula form a needle 30 that, when it is not in use, is protected by a cap 29. Inside the hollow barrel 1, a hollow driving rod 5 is inserted that is adapted to house a spring 6 kept stretched inside its rod by a closing plug 7 and by an extracting element 8 that can slide inside the driving rod 5.

As can better be seen in FIGS. 4 and 4a, the extracting element 8 has an annular notch 9 in which an annular sealing gasket 10 (O-Ring type) is inserted, of such a size as to seal against the internal wall of the hollow barrel 1 both when sucking and when compressing the liquid to be injected.

The extracting element 8 with related sealing gasket 10 (O-Ring type) therefore operates as a sucking and compressing piston.

The extracting element 8 moreover provides for a plane part 11 on whose face a female engaging notch 12 is inserted for the hub 3. The hub 3 (that is the male element) is better shown in FIGS. 5 and 5a.

On the external surface of the extracting element, a circular stop 13 is provided, adapted to abut against a circular step 14 obtained in the internal front part of the hollow driving rod 5.

With reference to FIGS. 5 and 5a, the hub 3 carrying the cannula 4 provides for a male engaging head 15 adapted to enter, at the end of the injection, into the female engaging notch 12.

The engaging head 15 has two deep longitudinal etchings 16 and 17 that are mutually orthogonal so that the cannula-holding hub is cut into four parts between the head 15 and a male circular undercut 18.

The cannula-holding hub further has a frustoconical surface 19 adapted to perform the seal with a corresponding female frustoconical surface 20 realized on the internal surface of the seat 2.

On the lower internal part of the hollow barrel 1, see FIGS. 7 and 7a, two small semicircular projections 21 and 22 are provided, that are able to press against the plane part 11 of the sliding extracting element and simultaneously to form a small circular recess 23 necessary for housing the annular sealing gasket 10 when, at the end of an injection, it is moved away from its female engaging notch, as will be better described below.

The internal surface of the seat 2 provides, under the projections 21 and 22, for a female annular groove or undercut 24 adapted to house the circular undercut 18.

The syringe operation will now be described. In the first step of sucking the liquid to be injected, that is obtained by extracting the hollow plunger from the hollow barrel 1, the sliding extracting element carrying the sealing gasket, O-Ring type, when the internal syringe vacuum would tend to suck it along the needle direction outside its operating position, is kept in its correct position by the circular stop 13 that will abut against the circular step 14 of the internal part on the front of the hollow driving rod.

When injecting the liquid, the sliding extracting element completed with sealing gasket, O-Ring type, when the internal syringe compression tends to make it go back inside the hollow driving rod outside its operating position, is kept in its correct position by the sealing gasket itself, engaged to the extractor and that abuts against the front part of the hollow driving rod.

The cannula-holding hub is always pushed, when assembling it, into the internal part of its seat in the hollow syringe barrel 1 and is only partially kept by interference between the two plastic surfaces.

The two components are perfectly integral one with the other, removing the inconvenience of a possible accidental disengagement, because the male circular undercut 18 on the cannula-holding hub engages the female annular groove 24 in the internal surface of the seat 2 of the hollow barrel 1.

Moreover, after their assembling, due to a small but important difference between the two positioning heights of the two undercuts 18 and 24 (the external female undercut will have to be slightly moved towards the needle tip in order to keep the corresponding internal male undercut pressurised towards it), the syringe liquid holding capacity is realised between the male frustum of cone 19 of the cannula-holding hub and the female frustum of cone 20 realised on the internal surface of the seat 2 of the hollow barrel 1 that always remain mutually pressurised.

The male engaging head 15 of the cannula-holding hub enters, at the end of the injection, into the female engaging notch 12 of the sliding extracting element. Its penetration and then the following engagement are made easier by the deep longitudinal etchings 16 and 17 that allow the head to be restricted and afterwards expanded to perform an efficient engagement of the hub to the extracting element.

The two semicircular projections 21 and 22, creating the circular recess 23, house the annular sealing gasket 10, O-Ring type, that, at the end of the injection, is moved away from its own annular notch 9 of the sliding extracting element to allow the needle, pulled by the spring, to go back to its protected position.

As the internal diameter of the female engaging notch 12 of the sliding extracting element is less than the diameter of the male engaging head 15, at the end of the injection, during the insertion of the male engaging head in the female engaging notch, this head, due to its longitudinal etchings that make it resilient, is pressed in such a way as to free the male circular undercut 18 from its own female circular undercut or annular groove 24. The mechanical separation of the two undercuts 18 and 24, obtained by squashing, highly simplifies the needle extraction operation with the consequent advantage of being able to use much weaker springs 6, with a lower wire diameter, and therefore springs that are much softer and more silent when clicking and also less costly.

Moreover, always at the end of the injection, the two small semicircular projections 21 and 22, realised in order to contain and keep the sealing gasket, O-Ring type, will also find themselves in the condition of pressing (by reaction to the thrust of the operator's thumb on the hollow driving rod of the extracting element that, with the sealing ring gasket, forms a real syringe plunger) on the plane part 11 of the extracting element in such a way as to easily perform the needle extracting operation independently from the spring force.

The invention claimed is:

1. A self-locking safety disposable syringe with needle protection after use, comprising:

a hollow barrel (1) having at one end an internal seat (2);

a hub (3) carrying a cannula (4);

a hollow driving rod (5), housing a spring (6), disposed in the hollow barrel (1); and an extracting element (8) on the rod for extracting the hub (3) from the internal seat (2), wherein the extracting element (8) has an annular notch (9) in which an annular sealing gasket (10) is disposed, of such a size as to seal against the internal wall of the hollow barrel (1) both when sucking and when compressing the liquid to be injected; said extracting element (8) with said sealing gasket (10) operating as a sucking and compressing piston;

and wherein on the inside of said end of the hollow barrel (1) two small semicircular projections (21) and (22) are provided, that are able to press, by reaction to the thrust of an operator's thumb on the hollow driving rod (5) of the extracting element (8), against a flat part (11) of the sliding extracting element (8) and simultaneously to form a small circular recess (23) for housing the annular sealing gasket (10) when, at the end of an injection, said sealing gasket (10) separates from said annular notch (9).

2. A syringe according to claim 1, wherein on said flat part (11) a recess (12) is provided for a male engaging head (15) of the hub (3), at the end of the injection, said male engaging head (15) having two deep longitudinal slots (16) and (17) that are mutually orthogonal so that the cannula-holding hub (3) is cut into four parts between the head (15) and a male circular rib (18).

3. A syringe according to claim 2, wherein, under the projections (21) and (22), the internal surface of the seat (2) has a female annular groove (24) adapted to house the circular rib (18).

4. A syringe according to claim 3, wherein the internal diameter of the recess (12) of the sliding extracting element (8) is less than the diameter of the male engaging head (15) so that, at the end of the injection, during the insertion of the male engaging head (15) in the female engaging notch (12), the head (15), due to its longitudinal slots (16) and (17) that make it resilient, is pressed in such a way as to free the male circular rib (18) from said groove (24).

5. A syringe according to claim 3, wherein the female groove (24) is moved towards the needle tip in order to keep the male rib (18) pushed towards it, so that the syringe liquid holding capacity is provided between a male frustum of cone (19) of the hub (3) and a female frustum of cone (20) on the internal surface of the seat (2) of the hollow barrel (1) that always remain pressed together.

6. A syringe according to claim 1, wherein, on the external surface of the extracting element (8), circular stop (13) is provided, adapted to abut against a circular step (14) on an internal front part of the hollow driving rod (5).

7. A syringe according to claim 1, wherein said annular sealing gasket (10) is an O-ring.

* * * * *